United States Patent
Ono et al.

(10) Patent No.: US 8,740,923 B2
(45) Date of Patent: Jun. 3, 2014

(54) PUNCTURE DEVICE AND PUNCTURE NEEDLE CARTRIDGE

(75) Inventors: Nobue Ono, Okayama (JP); Toshiharu Tsubouchi, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/662,279

(22) Filed: Apr. 8, 2010

(65) Prior Publication Data

US 2010/0198246 A1    Aug. 5, 2010

Related U.S. Application Data

(63) Continuation of application No. 11/912,932, filed as application No. PCT/JP2006/308911 on Jul. 27, 2006, now abandoned.

(30) Foreign Application Priority Data

Apr. 28, 2005    (JP) .................................. 2005-132678
May 16, 2005    (JP) .................................. 2005-143272

(51) Int. Cl.
  *A61B 17/32*    (2006.01)

(52) U.S. Cl.
  USPC ........................................................ 606/182

(58) Field of Classification Search
  USPC ........... 600/564, 567; 606/181–182, 184–186, 606/188–189
  See application file for complete search history.

(56) References Cited

U.S. PATENT DOCUMENTS

| | | | |
|---|---|---|---|
| 5,314,442 A | 5/1994 | Morita | 606/182 |
| 5,554,166 A | 9/1996 | Lange et al. | |
| 5,628,764 A * | 5/1997 | Schraga | 606/182 |
| 5,868,772 A | 2/1999 | LeVaughn et al. | |
| 6,261,245 B1 | 7/2001 | Kawai et al. | 600/576 |
| 6,858,015 B2 | 2/2005 | List | |
| 2003/0144608 A1 | 7/2003 | Kojima et al. | 600/583 |
| 2004/0034318 A1 | 2/2004 | Fritz et al. | 604/19 |
| 2004/0131437 A1 | 7/2004 | Kasai et al. | |
| 2004/0193201 A1 | 9/2004 | Kim | 606/181 |
| 2004/0243165 A1 | 12/2004 | Koike et al. | 600/181 |

(Continued)

FOREIGN PATENT DOCUMENTS

| | | |
|---|---|---|
| EP | 1 570 783 | 9/2005 |
| EP | 2005342325 | 12/2005 |

(Continued)

*Primary Examiner* — Ashley Fishback
(74) *Attorney, Agent, or Firm* — Steptoe & Johnson LLP

(57) ABSTRACT

A puncture device is constituted such that a plunger (2) is provided with a lever (3) which is partially restricted in rotation, and a forward urging force is obtained by a contraction restorative force of a tension spring (4), and the tension spring (4) is again expanded with the lever (3) as a leverage when the plunger (2) further moves forward due to its inertia from a position where no urging force is not applied, and the plunger (2) is urged backward by a restorative force of the re-expansion. Further, a puncture needle cartridge is provided with a lancet body (203) having a puncture needle, and a puncture needle holder (201) in which the lancet body (203) is movably stored, and further, the lancet body (203) has an arm means (302) and the puncture needle holder (201) contains a to-be-latched means (303) that cooperates with the arm means (302). Thereby, the fabrication process is simplified, and plural times of punctures of the puncture needle is prevented, and further, the puncture speed is controlled, and moreover, the used puncture needle is discarded safely.

3 Claims, 11 Drawing Sheets

(56) References Cited

U.S. PATENT DOCUMENTS

| | | | |
|---|---|---|---|
| 2004/0260325 A1 | 12/2004 | Kuhr et al. | 606/181 |
| 2005/0070945 A1 | 3/2005 | Schraga | 606/182 |
| 2005/0131441 A1 | 6/2005 | Ilio et al. | |
| 2005/0149090 A1 | 7/2005 | Morita et al. | 606/181 |
| 2006/0008389 A1 | 1/2006 | Sacherer et al. | 422/102 |
| 2008/0082023 A1 | 4/2008 | Deck et al. | 600/583 |
| 2009/0012427 A1 | 1/2009 | Fukuzawa | 600/583 |
| 2009/0069717 A1 | 3/2009 | Kojima et al. | 600/583 |
| 2009/0069718 A1 | 3/2009 | Kojima et al. | 600/583 |
| 2009/0069719 A1 | 3/2009 | Kojima et al. | 600/583 |
| 2009/0088787 A1 | 4/2009 | Koike et al. | 606/182 |
| 2009/0093694 A1 | 4/2009 | Kojima et al. | 600/345 |
| 2009/0093736 A1 | 4/2009 | Kojima et al. | 600/583 |
| 2009/0105615 A1 | 4/2009 | Kojima et al. | 600/583 |
| 2009/0204139 A1 | 8/2009 | Morita et al. | 606/182 |
| 2010/0198246 A1 | 8/2010 | Ono et al. | |

FOREIGN PATENT DOCUMENTS

| | | |
|---|---|---|
| EP | 1 815 792 | 8/2007 |
| JP | 1-185245 | 7/1989 |
| JP | 06-133955 | 5/1994 |
| JP | 07-16218 | 1/1995 |
| JP | 10-192262 | 7/1998 |
| JP | 11/76212 | 3/1999 |
| JP | 2000-116768 | 4/2000 |
| JP | 2000-245717 | 9/2000 |
| JP | 2002-085384 | 3/2002 |
| JP | 2004-113580 | 4/2004 |
| JP | 2004-512129 | 4/2004 |
| JP | 2004-283568 | 10/2004 |
| JP | 2004-290390 | 10/2004 |
| JP | 2005-111135 | 4/2005 |
| JP | 2005-192713 | 7/2005 |
| JP | 2005-312763 | 11/2005 |
| JP | 2005-342325 | 12/2005 |
| JP | 2006-55190 | 3/2006 |
| JP | 2006-516723 | 7/2006 |
| JP | 2006-305143 | 11/2006 |
| JP | 2006-314718 | 11/2006 |
| JP | 2008-531156 | 8/2008 |
| WO | 02/567679 | 7/2002 |
| WO | WO 02/100251 | 12/2002 |
| WO | WO 02/100273 A1 | 12/2002 |
| WO | 03/005907 | 1/2003 |
| WO | WO 2004/054445 | 7/2004 |
| WO | 2004/080305 | 9/2004 |
| WO | 2006/046570 | 5/2006 |

\* cited by examiner

PUNCTURE DEVICE AND PUNCTURE NEEDLE CARTRIDGE

The present application is a Continuation application of Ser. No. 11/912,932, filed Jan. 10, 2008, which was a national stage entry of International Application PCT/JP2006/308911, filed Apr. 27, 2006, which claims priority to Japanese Patent Application Nos. 2005-132678, filed Apr. 28, 2005, and 2005-143272, filed May 16, 2005, the entire contents of which are hereby incorporated by reference.

TECHNICAL FIELD

The present invention relates to a puncture device to be used for collecting blood from a fingertip or the like in advance of analysis of the blood, and a puncture needle cartridge for replacement.

BACKGROUND ART

Conventionally, there have been invented various kinds of puncture devices for collecting blood from skins of human beings and animals for analysis of the blood. In recent years, a puncture device in which an urging force for puncture is charged simultaneously with attachment of a puncture needle to the puncture device has been invented (refer to Patent Document 1: Japanese Published Patent Application No. 2000-245717). Such puncture device performs operations of puncture and withdrawal using two compression springs, i.e., a first compression spring for puncture and a second compression spring for withdrawal. Further, a puncture needle cartridge for discarding a puncture needle which has touched the skin has been developed to avoid infection due to attached blood.

FIG. 10 is a cross-sectional view of a conventional puncture device 1100. In FIG. 10, a natural position of a plunger 1002 is restricted by the total length of a first compression spring 1000, and the plunger 1002 is urged toward a front end of the puncture device 1100 by a restorative force of the first compression spring 1000 during puncture, while it is urged toward a rear end of the puncture device 1100 by a restorative force of the second compression spring 1001 during withdrawal. A charge lever 1003 slides backward to attach a puncture needle 1004 to the puncture device, and simultaneously, it stores a urging force for puncture by using the first compression spring 1000 and the second compression spring 1001.

FIG. 11 is a cross-sectional view of a conventional puncture needle cartridge 1100. As shown in FIG. 11, the puncture needle cartridge 1101 comprises a puncture needle holder 1005, a lancet body 1007 having a puncture needle 1004, and a puncture needle protection cap 1006 for protecting the puncture needle 1004. The puncture needle holder 1005 houses the lancet body 1007. The lancet body 1007 is stored so as to be movable in the puncture needle holder 1005 along its axial direction. Further, the lancet body 1007 has a large diameter portion 1008 to prevent the lancet body 1007 from moving toward an opening of the puncture needle holder 1005, i.e., toward the front end, unless a predetermined force is applied.

The puncture needle cartridge 1101 constituted as described above is attached to the puncture device 1100, and the lancet body 1007 is inserted in the plunger 1002 of the puncture device 1100. When performing puncture, this plunger 1002 is moved by an urging means, and thereby the lancet body 1007 projects toward the front end and the puncture needle 1004 protrudes from the opening of the puncture needle holder 1005, and thus the puncture site. After the puncture, when the puncture needle 1004 is removed from the puncture site, the lancet body 1007 is moved in a direction opposite to the forward direction (i.e., toward the rear end) by the urging means of the puncture device 1100, and thereby the puncture needle 1004 is again housed in the puncture needle holder 1005.

DISCLOSURE OF THE INVENTION

Problems to be Solved by the Invention

When two compression springs are used as in the conventional puncture device shown in FIG. 10, it is necessary to secure precision of the total length of the first compression spring 1000 that determines the natural position of the plunger 1002. However, as is well known, it is very difficult to secure precision of a total length of a compression spring because of its configuration. Therefore, in order to secure precision of the product, it is necessary to obtain a required measure by such as accurately polishing the both ends of the first compression spring 1000. Further, it is also necessary to consider distribution between a force that enables puncture and a force that reliably returns the puncture needle, and an advanced technique for optimizing a ratio of spring pressures between the first compression spring 1000 and the second compression spring 1001 is required. Further, when two compression springs are used as means for urging the plunger 1002, reciprocation of the plunger due to the compression springs (i.e., howling) undesirably occurs, and this howling causes that the needle punctures the skin several times, leading to an increase in pain that inflicts suffering on the patient. Further, according to a recent survey of patients, not only pain during puncture but also impact sound of the puncture device further increase fears of the patients.

Further, although replacement of the puncture needle is safely carried out by using the conventional puncture needle cartridge 1101 shown in FIG. 11, the puncture needle cartridge 1101 is constituted such that the once used puncture needle 1004 can be reused. That is, since the puncture needle cartridge 1101 which is once removed from the puncture device can be again attached to the puncture device, the puncture needle 1004 can be projected from the opening of the puncture needle holder 1005 many times so long as an urging force is stored by reattachment. Therefore, the once used puncture needle 1004 is reused without replacement, leading to a possibility of infection or the like.

Further, when the puncture needle cartridge 1101 shown in FIG. 11 is attached to the puncture device 1000, the puncture needle 1004 might be projected unless it is covered with the puncture needle protection cap 1006. Further, the lancet body 1007 is provided with the large diameter part 1008 so that the lancet body 1007 cannot be moved unless a predetermined force is applied thereto. However, the puncture needle cartridge 1101 which has once performed a puncture operation is released from the locking by the large diameter part 1008, and the puncture needle 1004 might be projected from the opening of the puncture needle holder 1005 if the puncture needle cartridge 1101 removed from the puncture device is turned downward, resulting in a problem that it is dangerous to discard the cartridge 1101 without a cap.

The present invention is made to solve the above-described problems and has for its object to simplify the fabrication process of a puncture device, and provide a puncture device and a puncture needle cartridge which can prevent plural times of punctures of a puncture needle, can adjust the puncture speed, and further, can safely discard a used puncture needle.

Measures to Solve the Problems

In order to solve the above-mentioned problems, according to Claim 1 of the present invention, there is provided a puncture device comprising: a housing having an opening at its front end, and a plunger which is held in the housing, slidably in forward and backward directions of the housing, which plunger holds a puncture needle detachably; and a tension spring which urges the plunger in its forward and backward directions; wherein the plunger is provided with a lever that is rotatable within a predetermined range, around a rotation shaft that is provided on the plunger; a front end of the tension spring is fixed to a first tension spring fixing chip that is fixed in the housing; a rear end of the tension spring is latched by a second tension spring fixing part that is provided on the rotatable lever; the second tension spring fixing part moves backward in conjunction with backward movement of the plunger, and expands the tension spring in an axial direction of the puncture device; the tension spring urges the plunger toward the front end of the housing via the second tension spring fixing part and the lever, by a restorative force that is caused by the expansion of the tension spring in its axial direction; and when the plunger moves toward the front end of the housing due to the urging force toward the front end, a fulcrum shaft provided on the housing contacts a peripheral edge portion of the rotatable lever, which is located between the rotation axis and the second tension spring fixing part, and the plunger further moves forward due to its inertial force even after the contact and thereby the fulcrum shaft pushes the rotatable lever backward, whereby the tension spring is again expanded via the rotatable lever and urges the plunger toward the rear end by its restorable force that occurs due to the re-expansion.

Further, according to the present invention, in the puncture device, the plunger has a first projection; the housing has a lock plate that engages with the first projection; urging of the plunger toward the front end of the housing by the restorative force that occurs due to expansion of the tension spring in its axial direction is restricted by that the first projection and the lock plate are engaged with each other; and when the engagement of the first projection with the lock plate is released by moving the lock plate with an external operation, the tension spring moves the plunger toward the front end of the housing by its urging force toward the front end.

According to the present invention, the puncture device further includes a puncture speed control mechanism for adjusting the restorative force of the tension spring by changing the position of the lock plate in the axial direction, thereby to control a puncture speed.

According to the present invention, the puncture device further includes a puncture needle cartridge injection mechanism for injecting a puncture needle cartridge, which mechanism has an injection rod that contacts an internal end surface of the puncture needle cartridge in the housing after the puncture operation is completed, and pushes out the cartridge.

According to the present invention, there is provided a puncture needle cartridge which is constituted by a lancet comprising a lancet body having a puncture needle and a puncture needle protection cap for protecting the puncture needle, and a puncture needle holder which has an opening and holds the lancet body so that the lancet body is movable in the holder; wherein the lancet body further includes an arm means which is shaped such that one end thereof is connected to the lancet body while the other end is opened so as to be broadened toward the front end of the lancet body, and is elastically deformable outward or toward the center of the lancet body; the puncture needle holder is a cylindrical holder which has a to-be-latched means that operates in conjunction with the arm means, and holds the lancet body movably along its axial direction, from an initial position of the lancet body where the arm means is positioned behind the to-be-latched means or from a first position as a puncture preparation position to a second position where the puncture needle protrudes; the lancet body is constituted such that, when it moves from the first position along the puncture direction, the arm means operates in conjunction with the to-be-latched means of the puncture needle holder and elastically deforms outward the lancet body, and the to-be-latched means contacts the contact part at the one end of the arm means and thereby movement of the to-be-latched means in the puncture direction is stopped; when the puncture needle cartridge is inserted into the puncture device from the rear end of the lancet body, the arm means is engaged with the housing of the puncture device, and elastically deforms toward the center of the lancet body so that it does not cooperate with the to-be-latched means of the puncture needle holder, and thereby the lancet body moves from the first position to the second position to perform puncture operation; and after the puncture is completed, when removing the puncture needle cartridge from the puncture device, the puncture needle cartridge is pulled and thereby the lancet body and the puncture needle holder move apart from each other, and the lancet body returns to the first position from the third position as a puncture end position, and when the puncture needle cartridge is further pulled, the engagement of the arm means with the housing of the puncture device is released as well as the elastic deformation of the arm means toward the center of the lancet body is released.

According to the present invention, in the puncture needle cartridge, the to-be-latched means is formed of a convex part that is provided inside the puncture needle holder; the puncture needle protection cap protects the puncture needle, and fixes the lancet body so that the lancet body does not move in the puncture needle holder when the puncture needle cartridge is inserted in the puncture device; when the puncture needle cartridge having the puncture needle protection cap is inserted in the puncture device, the lancet body is fixed so as not to move in the puncture needle holder, and the arm means is engaged with the housing of the puncture device and thereby the arm means elastically deforms toward the center of the lancet body; and when the puncture needle cartridge from which the puncture needle protection cap is removed is inserted in the puncture device, the lancet body and the puncture needle holder move so as to approach each other, and the arm means and the convex portion of the to-be-latched means cooperate with each other, whereby the arm means elastically deforms outward from the lancet body.

According to the present invention, in the puncture needle cartridge, the lancet body has a first convex portion on its trunk portion while the puncture needle holder has, in its axial direction, a groove that fits to the first convex portion, and the groove guides the first convex portion, whereby the lancet body moves in the puncture needle holder along, its axial direction.

According to the present invention, in the puncture needle cartridge, the lancet body further has, on a rear end of the trunk portion, a second convex portion that operates in conjunction with the rear end surface of the puncture needle holder.

According to the present invention, the puncture needle cartridge is constituted such that the lancet is incorporated in the puncture needle holder; the second convex portion comprises an elastically deformable material, and has a shape that inclines toward the rear end of the trunk portion of the lancet body; and when the lancet is incorporated in the puncture needle holder, the rear end of the lancet is inserted from the front end of the puncture needle holder so that the second convex portion is elastically deformed.

Effects of the Invention

According to the puncture device of the present invention, an end of the tension spring is fixed while the other end thereof is latched to a front end of the lever that is fixed to the plunger movably within a predetermined range, and the lever is moved backward in conjunction with backward move of the plunger to expand the tension spring in its axial direction, and the plunger can be urged toward the front end by a restorative force that is caused by the expansion of the spring. When the lever moves up to a position where it contacts the fulcrum, the rotatable lever rotates around the rotation shaft that is provided on the plunger, and thereby the plunger further moves toward the front end and the tension spring is expanded via the rotatable lever, and the plunger can be urged toward the rear end by a restorative force of the spring. In this way, the means for urging the plunger toward the front end and the rear end is realized by one tension spring, whereby the fabrication process of the puncture device is simplified, and plural times of punctures by the puncture needle is avoided.

Further, the puncture speed is controlled by controlling the urging force with varying the position of the lock plate, whereby the puncture speed is optimized to reduce the degree of feeling pain.

Further, since adoption of a puncture needle having a case is combined with an injection mechanism, the user can discard the puncture needle after performing puncture without touching the puncture needle and a portion (case) that has been applied to the skin, thereby preventing infection and injury by the puncture needle to enhance the safety.

Further, the puncture needle cartridge according to the present invention is provided with the lancet body having the puncture needle, and the puncture needle holder, and the lancet body has the arm means while the puncture needle holder has the to-be-latched means that cooperates with the arm means, and movement of the lancet body in the puncture direction is stopped when the arm means and the to-be-latched means cooperate with each other. Therefore, projection of the puncture needle can be limited to only when puncture is carried out, thereby enhancing the safety of the puncture needle cartridge.

Further, when the puncture needle cartridge that has once been used, from which the puncture needle protection cap is removed, is attached to the puncture device, the arm means of the lancet body and the to-be-latched means of the puncture needle holder cooperate with each other, thereby preventing reuse of the once-used puncture needle.

Further, the puncture needle holder groove guides the first convex portion of the lancet body and thereby the lancet body moves in its axial direction in the puncture holder. Therefore, the lancet body moves more straightly in the puncture needle holder, resulting in a reduction in pain.

Further, since the second convex portion which cooperates with the rear end surface of the puncture needle is provided on the rear end of the trunk portion of the lancet body, the lancet body is prevented from dropping out of the puncture needle holder, thereby enhancing the safety.

Further, the second convex portion comprises an elastically deformable material and has a shape that inclines toward the rear end of the trunk portion of the lancet body, and when the lancet is incorporated in the puncture needle holder, the rear end of the lancet is inserted from the front end of the puncture holder so that the second convex portion is elastically deformed. Therefore, the man-hour in assembling the puncture needle cartridge can be reduced.

BRIEF DESCRIPTION OF THE DRAWINGS

FIG. 1($b$) is a diagram illustrating the construction of a puncture device according to a first embodiment of the present invention.

FIG. 9($b$) is a cross-sectional view illustrating the internal structure of the puncture device in the puncture standby state, to which the puncture needle cartridge according to the second embodiment is attached.

FIG. 9($c$) is a cross-sectional view illustrating the internal structure of the puncture device during puncture, to which the puncture needle cartridge according to the second embodiment is attached.

FIG. 9($d$) is a cross-sectional view illustrating the internal structure of the puncture device after puncture, to which the puncture needle cartridge according to the second embodiment is attached.

FIG. 9($e$) is a cross-sectional view of the puncture device when the puncture needle cartridge according to the second embodiment is discarded.

FIG. 9($f$) is a cross-sectional view illustrating the internal structure of the puncture device when the once-used puncture needle cartridge from which a puncture needle protection cap is removed is attached to the puncture device.

DESCRIPTION OF REFERENCE NUMERALS

Figure 1A:
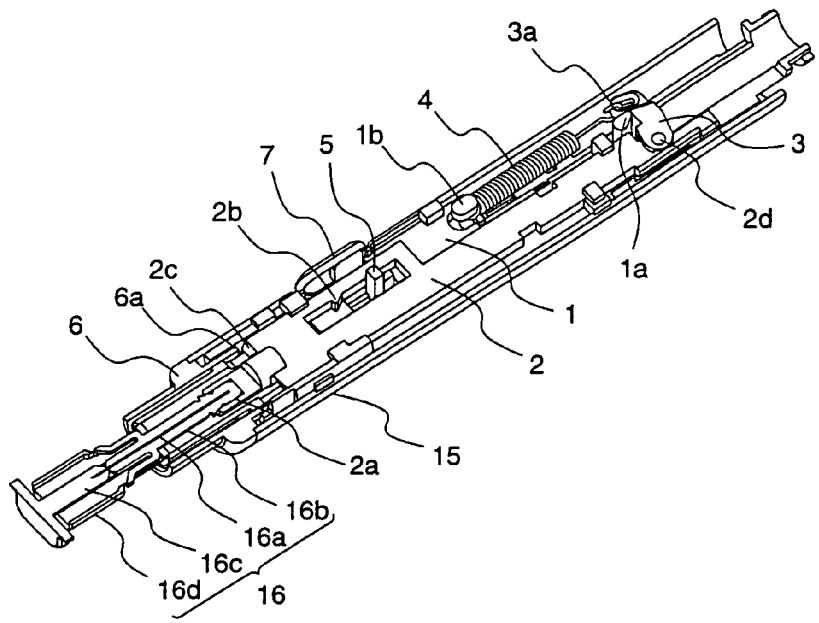
FIG. 1($a$) is a diagram illustrating the construction of a puncture device according to a first embodiment of the present invention.

1 . . . base plate
1$a$ . . . fulcrum shaft

1b... first tension spring fixing chip
2... plunger
2a... puncture needle holding part
2b... first projection
2c... sliding restriction part
2d... rotation axis
3... lever
4... tension plate
5... lock plate
5a... lock position adjusting projection
6... depth adjustment knob
6a... receiver
7... operation button
8... speed adjusting knob
8a... groove
9... ejection rod
10... ejection rod spring
12... ejection knob
13... ejection lock claw
14... lock claw spring
15... housing
15b... opening
16... puncture needle cartridge
16a... puncture needle
16b... lancet body
16c... puncture needle protection cap
16d... puncture needle holder
101... puncture device
102... puncture needle cartridge
201... puncture needle holder
202... puncture needle protection cap
203... lancet body
204... lancet
205... puncture needle holder internal diameter part
301... puncture needle
302... arm means
303... lancet body first convex portion
304... lancet body second convex portion
305... latch part
306... front end part
307... puncture needle protection part
401... opening
402... skin contact part
403... to-be-latched means
404... puncture needle holder groove
405... puncture needle holder rear end surface
601... plunger
602... housing
603... puncture needle holder cover
604... knurling shape
605... inner diameter of to-be-latched means
606... inner diameter of housing
1000... first compression spring
1001... second compression spring
1002... plunger
1003... charge lever
1004... puncture needle
1005... puncture needle holder
1006... puncture needle protection cap
1007... lancet body
1008... large diameter part
1100... puncture device
1101... puncture needle cartridge

BEST MODE TO EXECUTE THE INVENTION (Embodiment 1)

A puncture device according to a first embodiment of the present invention will be described with reference to FIG. 1.

Figure 1B:
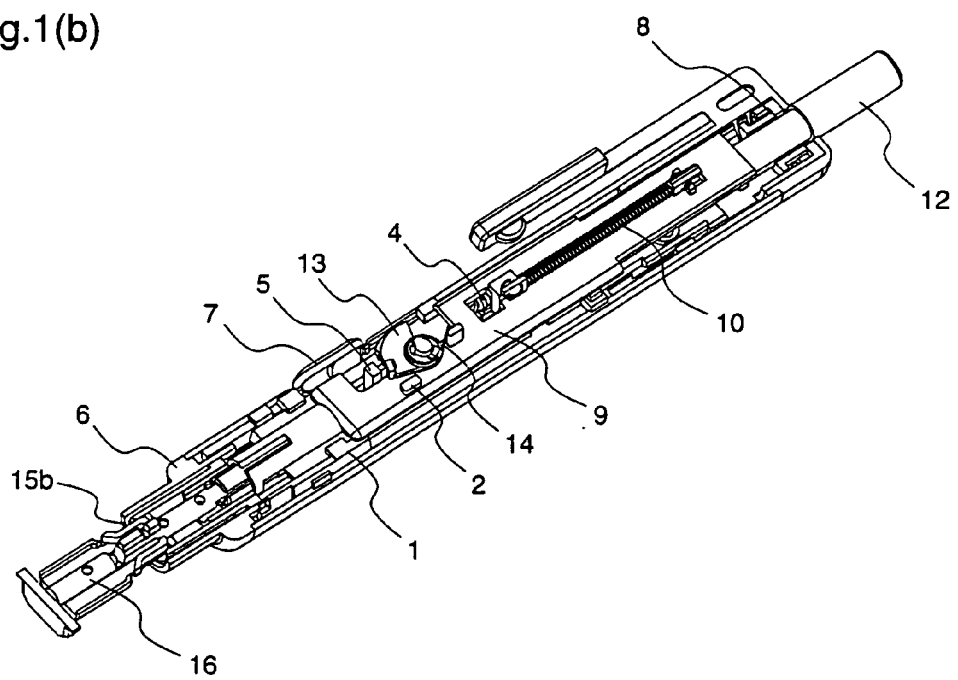

FIG. 1 is a diagram illustrating the construction of the puncture device according to the first embodiment. FIG. 1(a) is a cross-sectional view of the puncture device in a state where an ejection mechanism comprising an ejection rod 9, an ejection rod spring 10, an ejection knob 12, an ejection lock claw 13, and an ejection claw spring 14, is removed, and FIG. 1(b) is a cross-sectional view of the puncture device in a state where the ejection mechanism is attached.

In FIG. 1, the puncture device according to the first embodiment comprises a base plate 1 disposed inside a housing 15, and a plunger 2 that is slidably held by the base plate 1. The housing 15 and the base plate 1 may be integrated.

The housing 15 has, at its front end, an opening 15b in which the puncture needle cartridge 16 is inserted, and a needle depth adjustment knob 6 having a receiver 6a for restricting an amount of movement of the plunger 2 when the plunger 2 moves in its axial direction, is rotatably fitted to the opening 15b.

The receiver 6a of the needle depth adjustment knob 6 has a spiral shape, and the amount of movement of the plunger 2 in the axial direction can be varied by rotating the adjustment knob 6 with respect to the housing 15. While in FIG. 1 the receiver 6a and the needle depth adjustment knob 6 are integrated, these elements may be constituted by separated parts.

The plunger 2 comprises, from its front end, a puncture needle holding part 2a, a first projection 2b, and a sliding restriction part 2c.

The puncture needle cartridge 16 is detachably fitted to the puncture needle holding part 2a.

A lancet body 16b which holds a puncture needle 16a in a puncture needle holder 16d is slidably held in the puncture needle cartridge 16, and a puncture needle protection cap 16c which protects the puncture needle 16a is provided at a front end of the puncture needle 16a. Although the puncture needle protection cap 16c is removed when the puncture device is used, since the puncture needle 16a is positioned inside the puncture needle holder 16d, the user of the puncture needle does not see the needle and therefore can perform puncture without feeling fear.

The first projection 2b is a part of the plunger 2, and it is engaged with a lock plate 5.

The sliding restriction part 2c of the plunger 2 contacts against the receiver 6a, thereby restricting sliding of the plunger 2 toward the front end.

At the rear side of the plunger 2, a lever 3 is engaged with a rotation axis 2d so that it can rotate within a predetermined range, and a rear end of a tension spring 4, a front end of which is fixed to a first tension-spring fixing chip 1b, is engaged with a second tension-spring fixing chip 3a.

Hereinafter, a description will be given of the operation of performing puncture using the puncture device of the first embodiment which is constituted as described above, with reference to FIG. 2.

Figure 2:
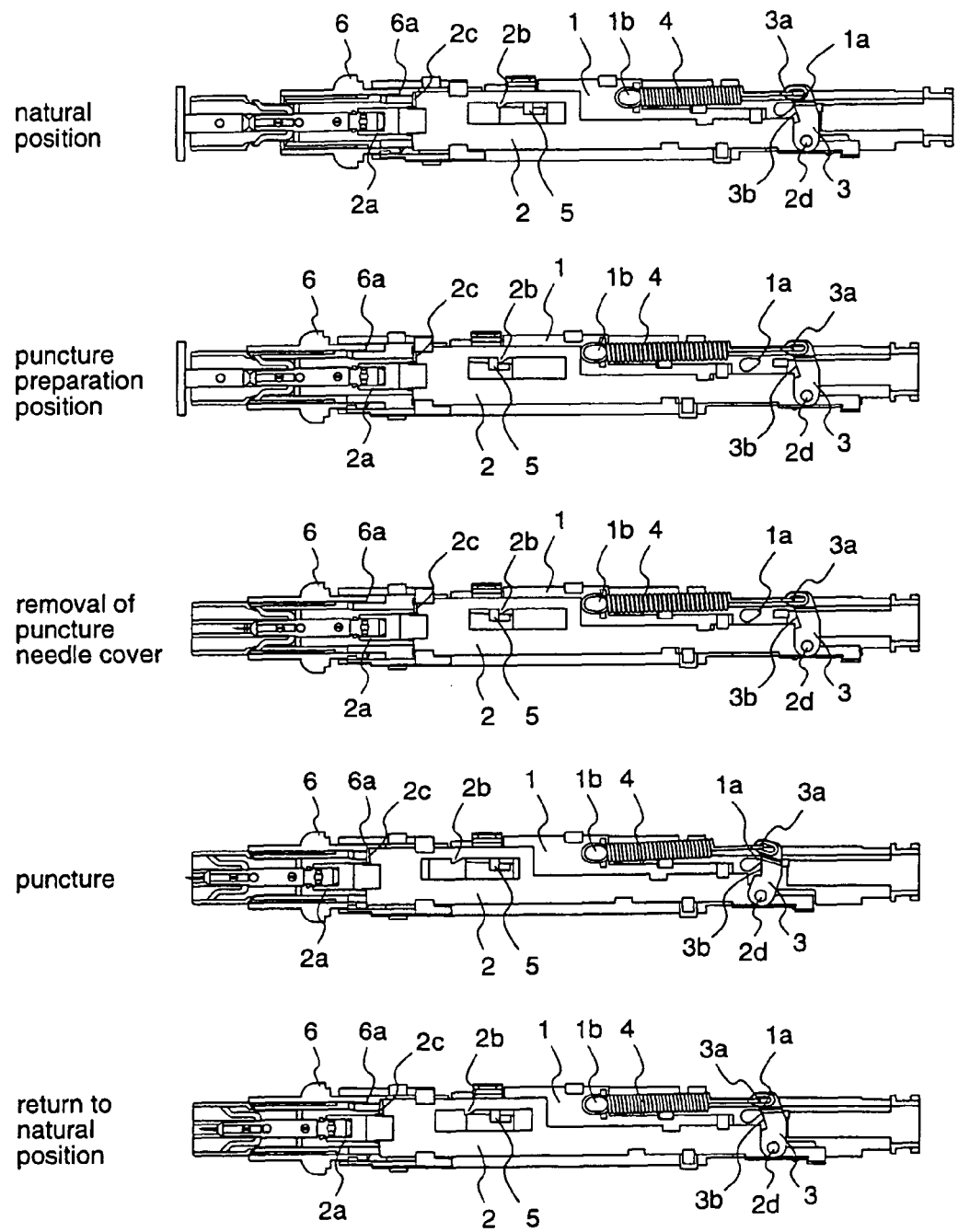
FIG. 2 is a diagram illustrating a motion of a plunger and a state of a tension spring according to the first embodiment.

FIG. 2 is a diagram illustrating the states of the tension spring 4 and the lever 3 when the plunger 2 is in a natural position, a puncture preparation position, and a puncture position.

In FIG. 2, the natural position is a position where the tension spring 4 moves the plunger 2 through the lever 3 toward the front end of the housing 15. The puncture preparation position is a position where the plunger 2 is urged toward the rear end of the housing 15 and thereby the plunger 2 is moved toward the rear end of the puncture device while expanding the tension spring 4 in its axial direction, and this motion of the plunger makes the first projection 2b and the lock plate 5 engage with each other and thereby urging of the plunger 2 toward the front end is stopped. The puncture position is a position where the engagement of the plunger 2 and the lock plate 5 is released and thereby the plunger 2 moves toward the front end due to an urging force toward the front end by the tension spring 4, and further, the plunger moves toward the front end exceeding the natural position due to an inertial force of the plunger 2.

In the state where the plunger 2 is in the natural position, the operator attaches the puncture needle cartridge 16 to the puncture needle holding part 2a of the plunger 2, and then presses the plunger 2 toward the rear end. When the plunger 2 moves toward the rear end, the lever 3 whose rotation to the left is restricted also moves toward the rear end in conjunction with the plunger 2, and thereby the tension spring 4 is extended in its axial direction.

When the plunger 2 is further pushed into the housing 15, the first projection 2b of the plunger 2 is engaged with the lock plate 5, and urging of the plunger 2 toward the front end is stopped, whereby the plunger is set in the puncture preparation position.

In the puncture preparation position, when the operator presses the operation button 7 provided on the housing 15, the lock plate 5 moves in the direction which releases the engagement with the first projection 2b and thereby the engagement is released, and the plunger 2 swiftly urged toward the front end by a restorative force of the tension spring 4.

When the plunger 2 and the lever 3 move toward the front end due to the urging by the tension spring 4 toward the front end, a fulcrum shaft 1a provided on the housing 15 contacts a peripheral edge part 3b of the rotatable lever 3, which is located between the rotation axis 2d and the second tension spring fixing part 3a. Even after the fulcrum shaft 1a contacts the peripheral edge part 3b, the plunger 2 still moves forward due to its inertia force. Since the plunger 2 thus moves forward and the fulcrum shaft 1a pushes down the rotatable lever 3 backward while rotating the lever 3 to the right, the tension spring 4 is again expanded via the rotatable lever 3, and the plunger 2 is urged toward the rear end by a restorative force of the re-expanded tension spring 4. After the plunger 4 returns to the natural position, it moves across the natural position up to the puncture position located ahead the natural position due to its inertia force, and performs puncture in this puncture position. Then, the plunger 2 is urged backward from the puncture position to return to the natural position, thereby completing the puncture operation.

During the above-mentioned operation, the urging force of the plunger 2 toward the front end is obtained as follows. That is, the tension spring 4 is expanded in its axial direction to move the plunger 2 toward the front end, and thereby the first projection 2b of the plunger 2 is engaged with the lock plate 5, and this engagement stops urging of the plunger 2 toward the front end. Since the urging force of the plunger 2 toward the front end at this time is determined by an amount of expansion of the tension spring 4, it can be adjusted by changing the position of the lock plate 5, and thereby the puncture speed can be controlled.

Figure 3:
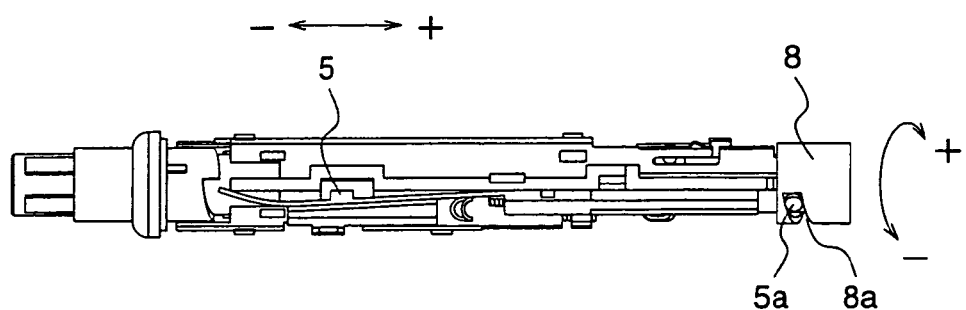
FIG. 3 is a diagram illustrating an example of a lock plate control mechanism (puncture speed control mechanism) according to the first embodiment.

Although there are considered various constructions of the puncture speed control mechanism which changes the position of the lock plate 5, an example is shown in FIG. 3.

In FIG. 3, a lock position control projection 5a is connected to the lock plate 5. Therefore, by constituting a mechanism for engaging the lock position control projection 5a with a spiral groove 8a of a speed control knob 8, the position of the lock position control projection 5a in the axial direction can be varied by turning the speed control knob 8, thereby to move the position of the lock plate 5 forward and backward with respect to the housing 15.

Although it is said that the pain during puncture depends on the puncture speed, the straightness of movement of the puncture needle, and the shape of the needle tip, it is possible to provide a puncture device that can reduce the pain by controlling the puncture speed using the above-mentioned puncture speed control mechanism.

After the puncture operation is ended, as shown in FIG. 1(b), the inner end surface of the puncture needle cartridge 16 is pushed forward from the housing 15 by the ejection rod 9 that is urged by the ejection rod spring 10 via the ejection knob 12, whereby the user can remove the puncture needle cartridge 16 from the puncture device without touching it.

The ejection lock claw 13 and the lock claw spring 14 are means for locking the puncture needle cartridge ejection mechanism against the urging force of the ejection rod spring 10, and this ejection lock state is released by the ejection knob 12 to perform ejection.

Further, when the puncture needle cartridge 16 is pushed forward from the housing, the front end of the injection rod 9 contacts the rear end of the puncture needle holder 16d and pushes the cover forward from the housing, whereby the puncture needle cartridge 16 can be pushed out with the puncture needle 16a being housed in the back of the puncture needle holder 16d, and thus safety of the detached puncture needle cartridge 16 can be ensured.

As described above, according to the puncture device of the first embodiment, the front end of the tension spring 4 is fixed to the housing 15 via the first tension spring fixing chip 1b while the rear end of the tension spring 4 is engaged with the second tension spring fixing part 3a of the lever 3 that is engaged with the plunger 2 rotatably within a predetermined range, and the rear end of the tension spring 4 is moved toward the rear end of the puncture device in conjunction with the movement of the plunger 2 toward the rear end of the puncture device to expand the spring 4 in its axial direction, whereby the plunger 2 can be moved toward the front end of the housing 15 via the second tension spring fixing part 3a by a restorative force caused by the expansion of the tension spring 4. Further, when the plunger 2 is moved beyond the natural position toward the front end, the tension spring 4 is again expanded by the function of the rotatable lever 3 that contacts the fulcrum shaft 1a, and the plunger 2 can be urged toward the rear end by a restorative force of the tension spring 4. In this way, the means for urging the plunger forward and backward is realized by one tension spring. Further, by changing the position of the fulcrum to be a center of fluctuation of the lever to change the ratio of the arm length of the lever, an optimum urging force toward the rear end can be obtained by the same tension spring, whereby the fabrication process of the puncture device is simplified, and plural times of punctures of the puncture needle is avoided.

(Embodiment 2)

Hereinafter, a puncture needle cartridge according to a second embodiment of the present invention will be described with reference to FIGS. 4 to 9.

Figure 4:
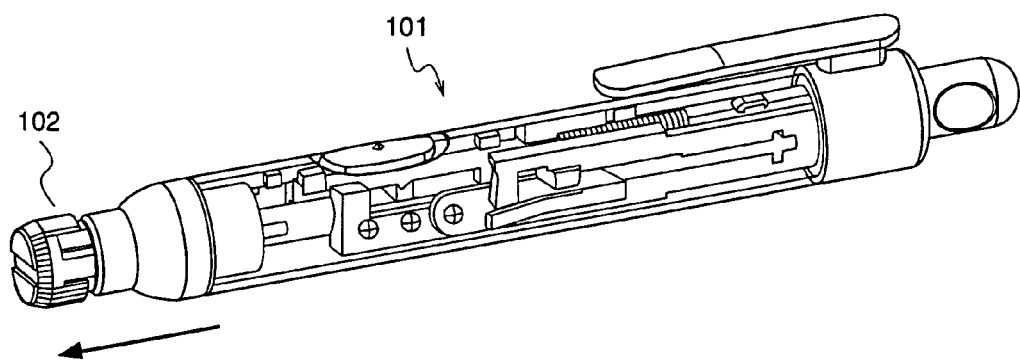
FIG. 4 is a diagram illustrating an example of a puncture device for performing puncture, which is provided with a puncture needle cartridge according to a second embodiment of the present invention.

FIG. 4 is a diagram illustrating an example of a puncture device which performs puncture with a puncture needle cartridge according to the second embodiment being attached thereto. As shown in FIG. 4, the puncture needle cartridge 102 according to the second embodiment is attached to the puncture device 101. It is assumed that a direction in which a puncture needle is projected (an arrow direction in FIG. 4) is a direction toward a front end, and a direction opposite to the front-end direction (a direction opposite to the arrow direction in FIG. 4) is a direction toward a rear end.

Next, the specific construction of the puncture needle cartridge 102 will be described with reference to FIGS. 5, 6, and 7.

Figure 5:
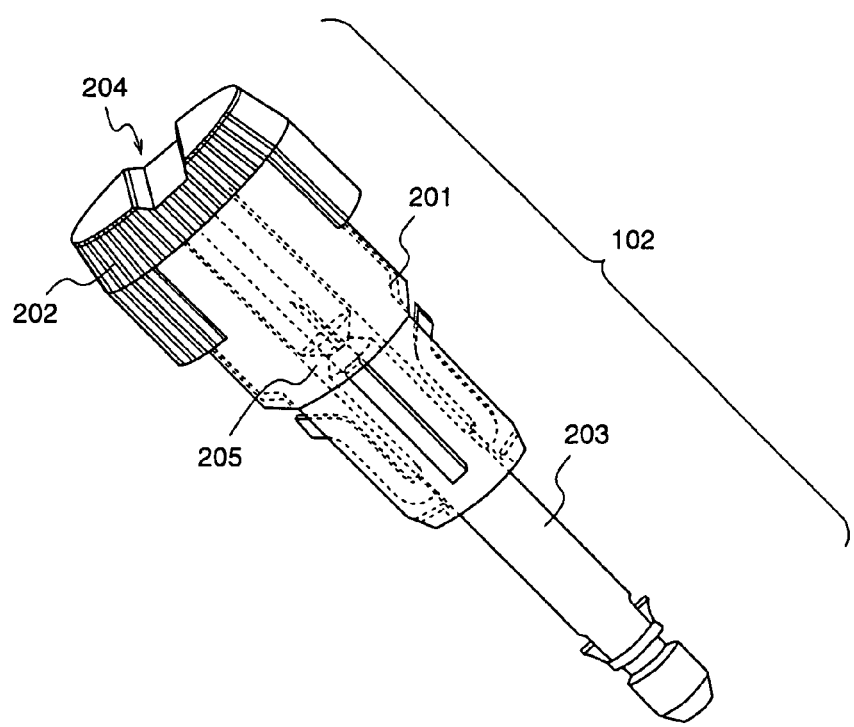
FIG. 5 is a diagram illustrating the construction of the puncture needle cartridge according to the second embodiment.

FIG. 5 is a configuration diagram illustrating the puncture needle cartridge according to the second embodiment. In FIG. 5, the puncture needle cartridge 102 has a puncture needle holder 201, a puncture needle protection cap 202, and a lancet body 203. The puncture needle protection cap 202 covers the puncture needle of the lancet body 203, and a lancet 204 comprising the puncture needle protection cap 202 and the lancet body 203 is stored in an inner-diameter part 205 of the cylindrical puncture needle holder 201. In the puncture needle cartridge 102 according to the second embodiment, the lancet body 203 is housed movably in its axial direction in the puncture needle holder 201 so that the puncture needle can be projected.

Next, the puncture needle holder 201 and the lancet 204 constituting the puncture needle cartridge 102 shown in FIG. 5 will be described with reference to FIGS. 6 and 7.

Figure 6:
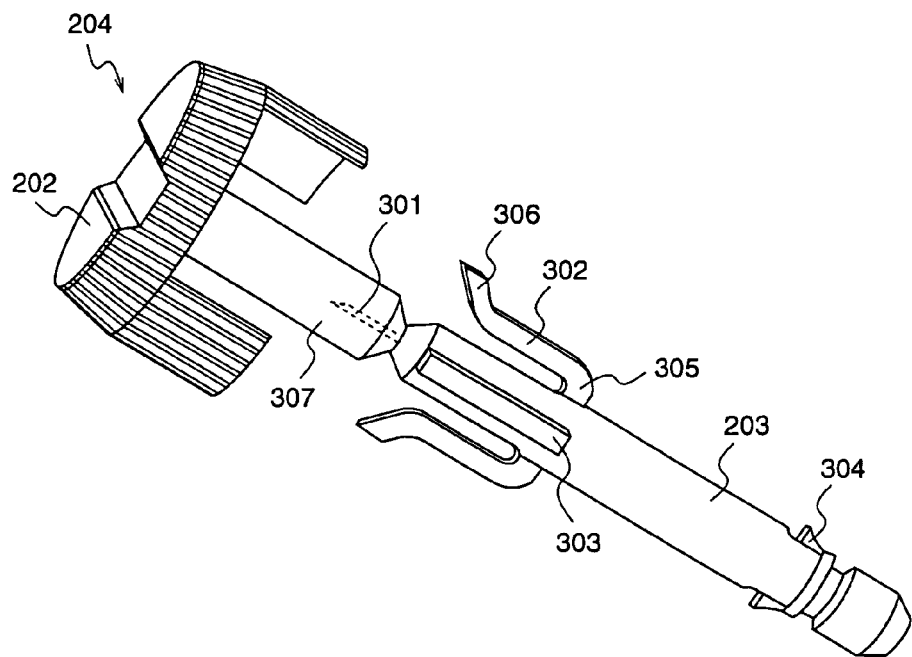
FIG. 6 is a diagram illustrating the construction of a lancet of the puncture needle cartridge according to the second embodiment.

FIG. 6 is a diagram illustrating the construction of the lancet 204. In FIG. 6, the lancet 204 comprises the lancet body 203 having a puncture needle 301, and the puncture needle protection cap 202 for protecting the puncture needle 301, and the puncture needle 301 is protected by a puncture needle protection part 307 of the puncture needle protection cap 202, which has the same shape as the trunk of the lancet body 203. Further, the lancet body 203 has an arm means 302, a lancet body first convex portion 303, and a lancet body second convex portion 304.

The arm means 302 has a latch part 305 as one end thereof being connected to the lancet body 203, and a front end part 306 as the other end thereof being opened such that it is tapered toward the front end of the lancet body 203. The arm means 302 elastically deforms toward the center of the lancet body 203 or outward from the lancet body 203.

The first convex portion 303 is shaped in a long strip, and it is provided in two positions at right and left toward the axial direction, on the trunk of the lancet body 203. Further, a second convex portion 304 is provided in two positions at right and left toward the axial direction, on the rear end of the trunk of the lancet body 203.

Figure 7:
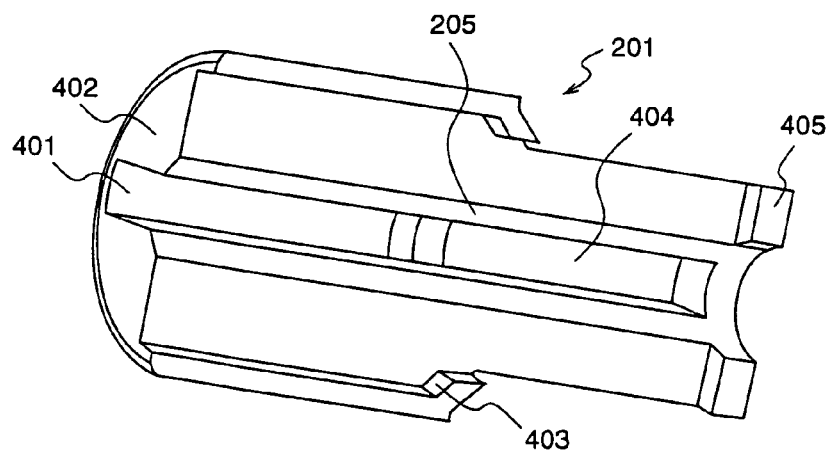
FIG. 7 is a cross-sectional view illustrating a puncture needle holder of the puncture needle cartridge according to the second embodiment.

FIG. 7 is a cross-sectional view of the puncture needle holder 201.

As shown in FIG. 7, the puncture needle holder 201 has, at its front end, a skin contact part 402 having an opening 401, and has a to-be-latched means 403 having a convex portion inside, which convex portion cooperates with the arm means 302. Further, the puncture needle holder 201 has, in its axial direction, a puncture needle holder groove 404 which is engaged with the first convex portion 303 of the lancet body 203 and serves as a guide for making the lancet body 203 move more straightly. The puncture needle holder 201 has a puncture needle holder rear end surface 405 which cooperates with the lancet body second convex portion 304 of the lancet body 203 to prevent dropping of the lancet body 203 toward the front end.

While in this second embodiment each of the first and second convex portions is provided in two positions, respectively, the number of these convex portions is not restricted thereto, and for example, it may be provided in only one position.

Further, while the first convex portion is shaped in a long strip, the shape of the first convex portion is not restricted thereto, and it may be in any shape so long as the lancet body 203 is moved more straightly by the guide of the puncture needle holder groove 404.

Further, in this second embodiment, the lancet body 203 has the first and second convex portions, and the puncture needle holder 201 has the grooves that are engaged with the respective convex portions. However, conversely, the lancet body 203 may have grooves and the puncture needle holder 201 may have convex portions along their axial directions, respectively, and the grooves and the convex portions may be engaged with each other to make the lancet body 203 move more straightly.

Figure 8:
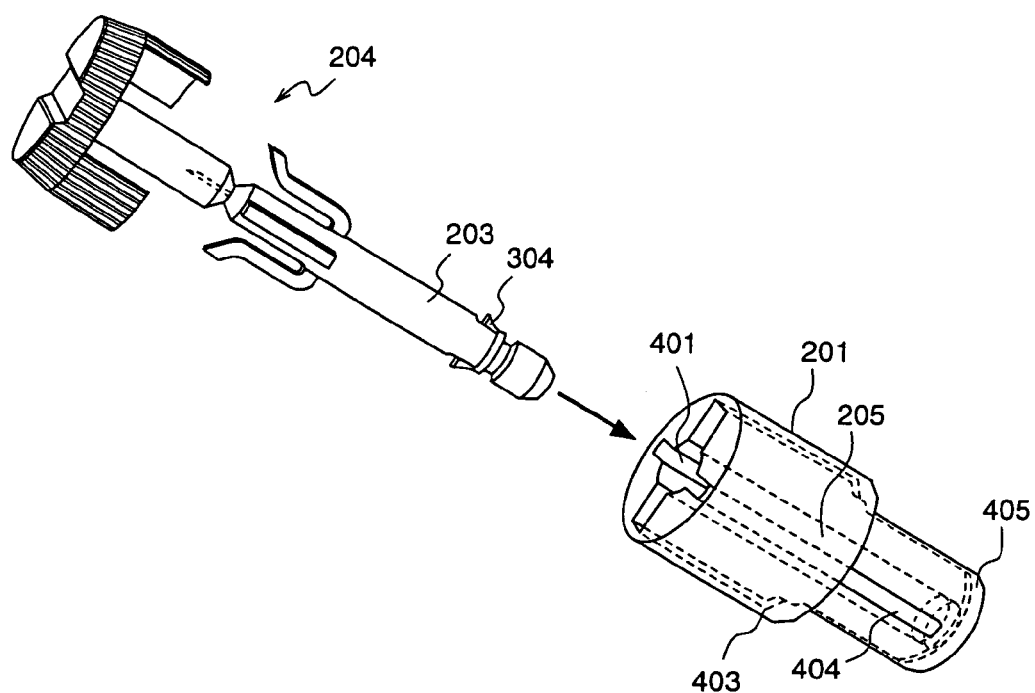
FIG. 8 is a diagram illustrating the puncture needle cartridge according to the second embodiment wherein the lancet is incorporated in the puncture needle holder.

Further, the puncture needle cartridge 102 shown in FIG. 5 is constituted by incorporating the lancet 204 in the inner-diameter part 205 of the puncture needle holder 201. At this time, as shown in FIG. 8, the rear end of the lancet body 203 is inserted from the opening 401 of the puncture needle holder 201. The second convex portion 304 comprises an elastically deformable material such as a resin. Further, the shape of the second convex portion 304 may be inclined toward the rear end of the trunk portion of the lancet body so that it can be easily inserted in the puncture needle holder 201, whereby the lancet body 203 can easily push the lancet 204 up to the position shown in FIG. 5 with the second convex portion 304 being elastically deformed. Thus, the lancet body can be easily incorporated in the puncture needle holder, and thereby the man-hour in assembling the puncture needle cartridge can be reduced. In this second embodiment, the position of the lancet body 203 where insertion of the lancet 204 in the puncture needle holder 201 is completed as shown in FIG. 5 is referred to as an initial position of the lancet body 203 (hereinafter, first position).

In the first position of the lancet body 203 where insertion of the lancet 204 in the puncture needle holder 201 is completed as shown in FIG. 5, when the lancet body 203 moves in the direction opposite to the puncture direction, the rear end of the arm means 302 and/or the first convex portion 303 contact the rear end portion 405 of the puncture needle holder, whereby the movement of the lancet body 203 in the direction opposite to the puncture direction is stopped. Further, also when the lancet body 203 moves in the puncture direction, the arm means 302 of the lancet body and the to-be-latched means 403 cooperate with each other, and the arm means 302 elastically deforms so as to broaden outward from the lancet body 203 and the latch part 305 of the arm means contacts the to-be-latched means 403, whereby the movement of the lancet body 203 in the puncture direction is stopped. Therefore, the puncture needle cartridge 102 according to the second embodiment can be constituted such that the puncture needle does not protrude when it is not attached to the puncture device and moves from the first position in the puncture direction.

Hereinafter, the puncture operation of the puncture needle cartridge constituted as described above will be described with reference to FIGS. 9(a) to 9(f).

Figure 9A:
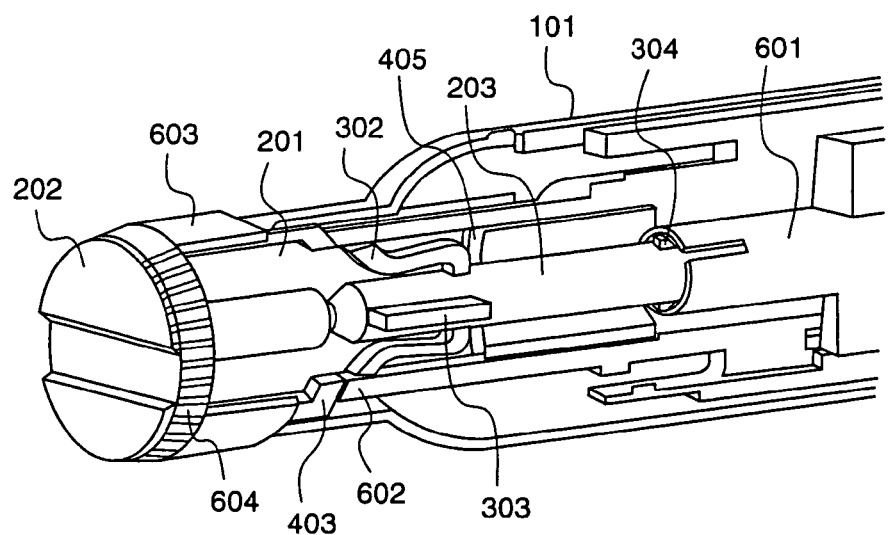
FIG. 9($a$) is a cross-sectional view illustrating the internal structure of the puncture device before puncture, to which the puncture needle cartridge according to the second embodiment is attached.
Figure 9B:
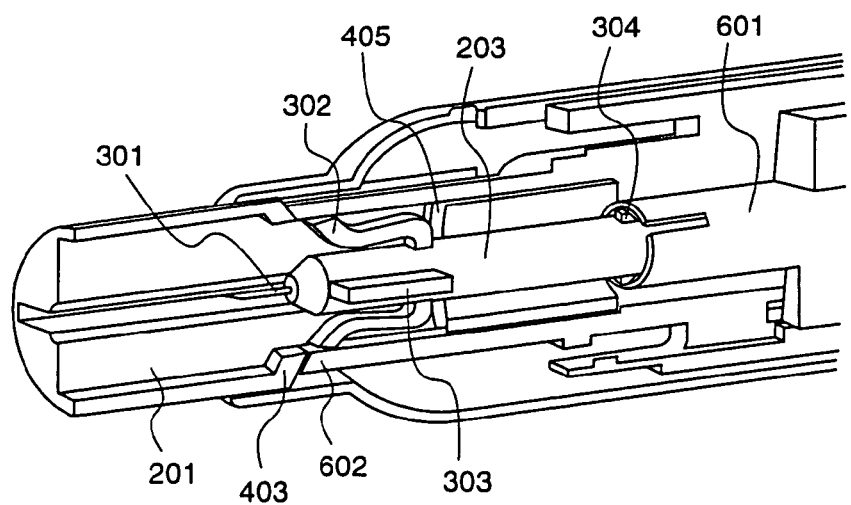
Figure 9C:
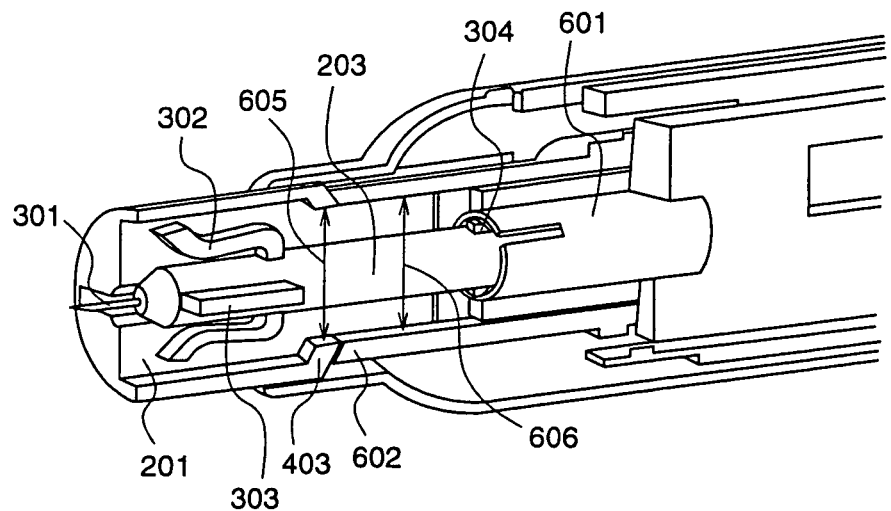
Figure 9D:
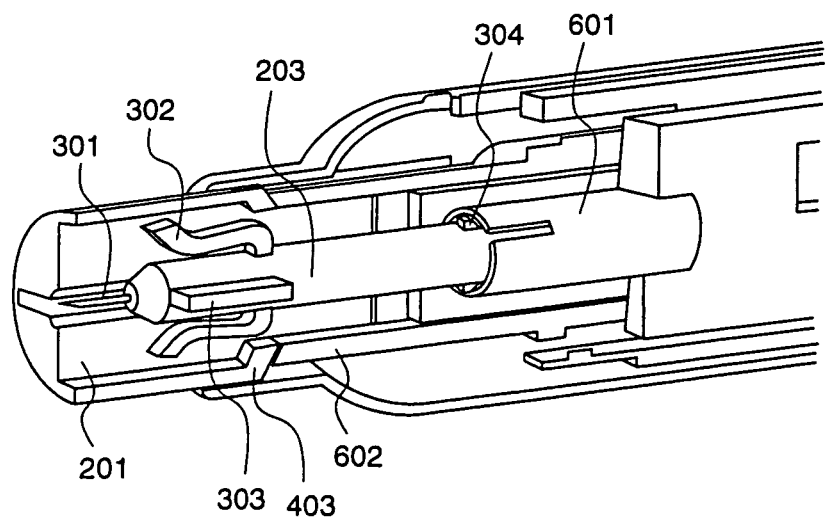
Figure 9E:
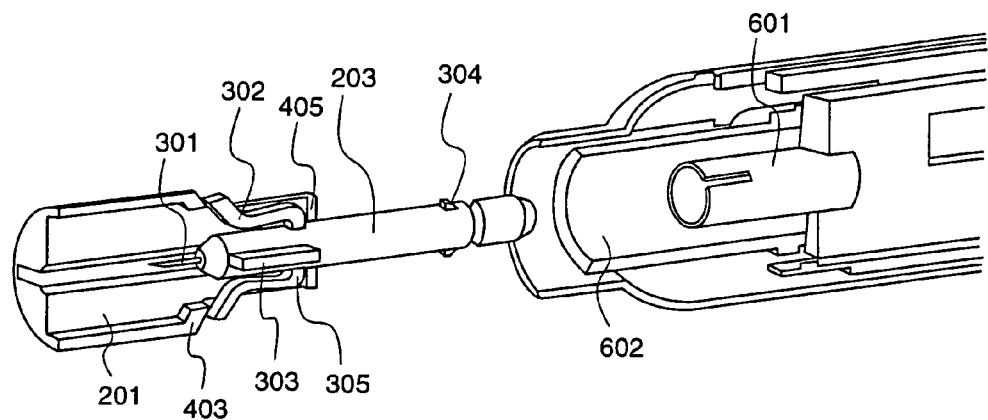

FIG. 9(a) is a cross-sectional view illustrating the internal structure of the puncture device before puncture, to which the puncture needle cartridge 102 according to the second embodiment is attached. FIG. 9(b) is a cross-sectional view illustrating the internal structure of the puncture device in the puncture standby state where the puncture needle protection cap 202 is removed. FIG. 9(c) is a cross-sectional view illustrating the internal structure of the puncture device in the position where the puncture needle is projected for puncture. FIG. 9(d) is a cross-sectional view illustrating the internal structure of the puncture device after puncture. FIG. 9(e) is a cross-sectional view illustrating the construction when the puncture needle cartridge 102 is removed from the puncture device and discarded.

First of all, the puncture needle cartridge 102 is inserted into the puncture device 101 as shown in FIG. 9(a), and the puncture needle protection cap 202 is removed from the state shown in FIG. 9(a) as shown in FIG. 9(b), thereby setting the puncture device 101 in the puncture preparation state where an urging force is stored by such as a charge spring (not shown) of the puncture device.

As shown in FIGS. 9(a) and 9(b), the positional relationship between the lancet body 203 of the puncture needle cartridge 102 and the puncture needle holder 201 before puncture is the same as that in the puncture standby state, that is, the arm means 302 is positioned behind the to-be-latched means 403, like the first position of the lancet body 203 shown in FIG. 5. In this way, the puncture needle cartridge 102 according to the second embodiment is attached to the puncture device 101 so that the first position wherein the arm means 302 is positioned behind the to-be-latched means 403 is the puncture preparation position, and the housing 602 of the puncture device grasps the rear end portion of the puncture needle holder 201, and the plunger 601 grasps the rear end portion of the lancet body 203.

At this time, the arm means 302 is elastically deformed toward the center of the lancet body by the housing 602 of the puncture device to stand by for puncture. That is, in the puncture needle cartridge shown in FIGS. 9(a) and 9(b), the arm means 302 and the housing 602 of the puncture device are engaged with each other, and the arm means 302 of the lancet body is elastically deformed toward the center of the puncture needle body as compared with FIG. 5.

Further, the puncture needle protection cap 202 is provided with a puncture needle holder cover 603 to make it easy to hold the protection cap when the puncture needle cartridge 102 is attached to the puncture device 101, and further, a portion of the puncture needle protection cap 202 to be held when the cap 202 is turned has a knurling shape 604 which makes the cap 202 fit to the hand and makes it easy to turn the cap 202 when it is twisted off.

While in this second embodiment the knurling shape 604 is adopted to make the puncture needle cap fit to the hand, the present invention is not restricted thereto, and an octagon shape or a finger shape may be adopted.

The puncture needle protection cap 202 protects the puncture needle. Further, in order to prevent the lancet body 203 from moving in the puncture needle holder, attachment of the puncture needle cartridge is performed while holding the puncture needle holder cover 603, whereby the arm means 302 and the housing 602 of the puncture device can be engaged with each other without mutually moving the puncture needle holder 201 and the lancet body 203. That is, since the puncture needle protection part 307 of the puncture needle protection cap 202 contacts the front end portion of the lancet body 203 in the inner-diameter part 205 of the puncture needle holder 201, the lancet body 203 can be fixed so as not to move in the puncture needle holder.

In the first position shown in FIG. 9(b), the user applies his/her finger or the like to the skin contact part 402 of the puncture needle holder 201, and pushes a puncture button (not shown) of the puncture device 101 to perform puncture.

At this time, as shown in FIG. 9(c), in the puncture needle cartridge 102, the plunger 601 shoots out the lancet body 203 from the first position by the urging force of the charge spring (not shown) of the puncture device, and the lancet body 203 and the plunger 601 move toward the front end, whereby the lancet body 203 moves to a position where the puncture needle protrudes (hereinafter referred to as "second position"). At this time, as shown in FIGS. 9(a) and 9(b), since the arm means 302 of the lancet body elastically deforms toward the center of the lancet body, the arm means 302 of the lancet body does not cooperate with the to-be-latched means 403 when the lancet body 203 moves toward the front end, whereby puncture can be carried out. Thereby, the puncture needle 301 protrudes from the opening 401 of the puncture needle holder 201, and punctures the puncture site. During the puncture, since the lancet body first convex portion 303 is engaged with the puncture needle holder groove 404, the lancet body 203 can move straightly in its axial direction.

The inner diameter 605 of the to-be-latched means 403 of the puncture needle holder may be constituted according to the inner diameter 606 of the housing of the puncture device to which the puncture needle cartridge is attached, and it should be constituted so that the arm means 302 does not cooperate with the to-be-latched means 403 when the lancet body 203 moves from the first position to the second position, i.e., the inner diameter 605 of the to-be-latched means 403 should be equal to or larger than the inner diameter 606 of the housing 602 of the puncture device.

Further, when the plunder 601 does not grasp the lancet body 203, the lancet body second convex portion 304 contacts the puncture needle holder rear end surface 405, thereby preventing the lancet body 203 from dropping out of the puncture needle holder 201.

Then, as shown in FIG. 9(d), in the puncture needle cartridge 102 after the puncture, the charge spring of the puncture device is restored to its original state, and thereby the lancet body 203 moves from the second position toward the rear end, and stops at a position where the puncture needle 301 does not protrude from the opening 401 of the puncture needle holder 201 although the position is closer to the front end than that when the cartridge 102 was attached. This position is the puncture end position (hereinafter referred to as "third position").

In the puncture needle cartridge 102 according to the second embodiment, the initial position of the lancet body 203 is regarded as the first position, and this first position is regarded as the puncture preparation position. However, the present invention is not restricted thereto. For example, a position behind the initial position may be regarded as the puncture preparation position in order to cope with a puncture device which once moves the plunger 601 and the lancet body 203 in a direction opposite to the puncture direction to charge a urging force during preparation for puncture. In this case, the same operation as mentioned above is performed with the puncture preparation position being set at the first position.

FIG. 9(e) is a diagram illustrating the puncture needle cartridge 102 when it is discarded.

After the puncture is ended, when removing the puncture needle cartridge 102, the user initially holds the puncture needle holder 201 in the state where the puncture needle cartridge 102 is as shown in FIG. 9(d), and pulls the puncture needle cartridge 102, whereby the puncture needle holder 201 and the lancet body 203 move apart from each other, and thereby the lancet body 203 moves from the third position back to the first position where the arm means 302 of the lancet body is positioned behind the to-be-latched means 403, and the latch part 305 of the arm means 302 of the lancet body contacts the rear end 405 of the puncture needle holder and/or the first convex portion 303 contacts the puncture needle holder groove 404. When the user further pulls the puncture needle cartridge 102, engagement of the lancet body 203 with the plunger 601 of the puncture device and engagement of the arm means 303 with the housing 602 of the puncture device are released, and elastic deformation of the arm means 302 toward the center of the lancet body is. released. Thus, in the state after the puncture needle cartridge is removed as shown in FIG. 9(e), the lancet body moves from the third position to the first position, and further, the arm means 302 that has been elastically deformed toward the center of the lancet body is restored to the original position. Therefore, even when the lancet body 203 is moved in the puncture direction in the puncture needle holder, the puncture needle does not protrude because the arm means 302 cooperates with the to-be-latched means 401. Thereby, the puncture needle cartridge can be safely discarded without requiring the puncture needle protection cap.

Figure 9F:
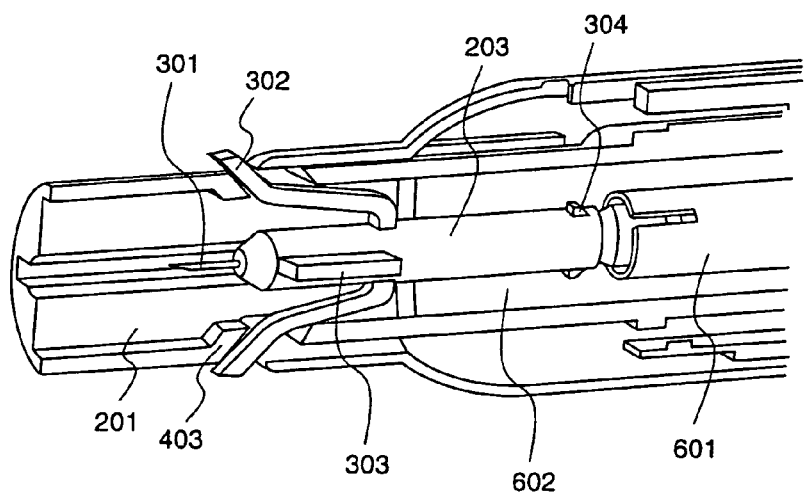
Figure 10:
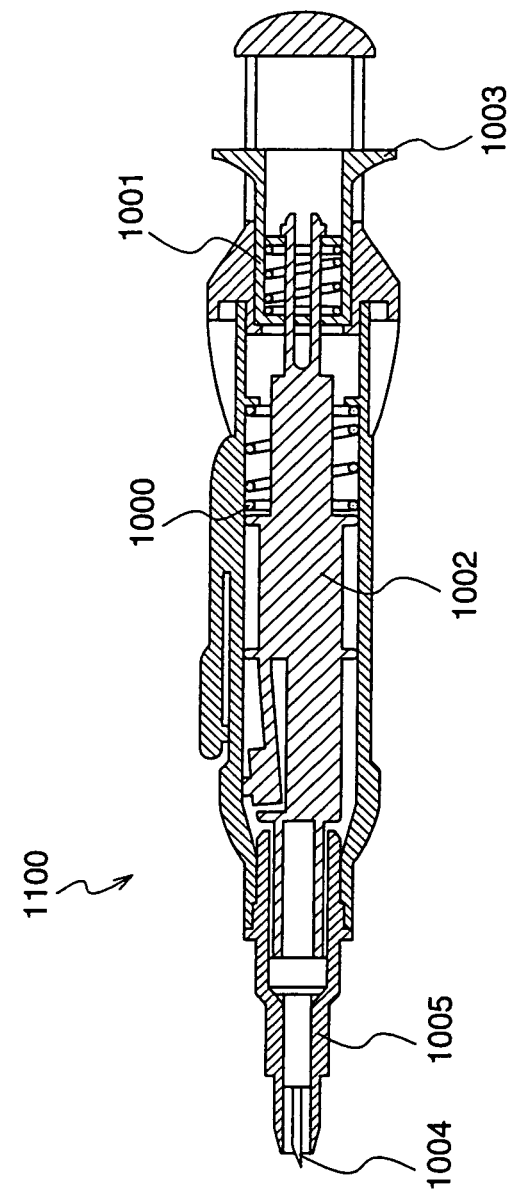
FIG. 10 is a cross-sectional view of the conventional puncture device.
Figure 11:
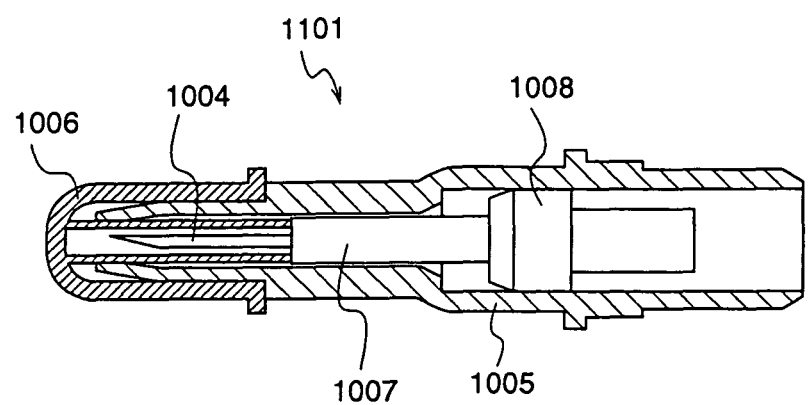
FIG. 11 is a cross-sectional view of the conventional puncture needle cartridge.

Next, a description will be given of the case where the arm means 302 of the lancet body and the to-be-latched means 403 cooperate with each other, with reference to FIG. 9(f). FIG. 9(f) is a diagram illustrating the internal structure where the arm means 302 and the to-be-latched means 403 cooperate with each other, and for example, it shows an internal structure of the puncture device when the user tries to insert the once-used puncture needle cartridge 102, from which the puncture needle protection cap 202 is removed, again into the puncture device 101. As shown in FIG. 9(f), when the user tries to insert the once-used puncture needle cartridge 102 from which the protection cap 202 is removed, into the puncture device 101, the puncture needle holder 201 and the lancet body 203 move so as to approach to each other, and the arm means 302 and the to-be-latched means 403 cooperate with each other, and thereby the arm means 302 elastically deforms outward. Thereby, the arm means 302 that extends outward contacts the insertion port of the puncture device or the housing, and the puncture needle cartridge 102 cannot be completely attached to the puncture device 101, and therefore, puncture cannot be performed again. That is, the puncture needle cartridge which has once performed puncture and then removed from the puncture device cannot be reused, and the puncture needle 301 never protrude from the cartridge.

It is needless to say that, even if the puncture needle has never been used, the puncture needle cartridge without the puncture needle protection cap cannot be attached to the puncture device, as in the case of FIG. 9(f). That is, since the puncture needle cartridge is constituted so that it cannot be attached to the puncture device when the puncture needle protection cap 202 is removed, a safer puncture needle cartridge can be provided.

As described above, the puncture needle cartridge according to the second embodiment makes the puncture needle 301 project only when puncture is to be performed, thereby preventing the puncture needle 301 from projecting from the opening 401 of the puncture needle holder at times other than puncture.

As described above, the puncture needle cartridge 102 according to the second embodiment is provided with the lancet body 203 having the puncture needle 301, and the puncture needle holder 201, and further, the lancet body 203 has the arm means 302 and the puncture needle holder 201 has the to-be-latched means 403 that cooperates with the arm means 302. When the arm means 302 and the to-be-latched means 403 cooperate with each other, movement of the lancet body 203 in the puncture direction is stopped. Therefore, projection of the puncture needle is limited to only when puncture is performed, and thereby safety of the puncture needle cartridge is enhanced. Further, when the once-used puncture needle cartridge 102 from which the puncture needle protection cap 202 is removed is attached to the puncture device 101, the arm means 302 of the lancet body 203 and the to-be-latched means 403 of the holder 201 cooperate with each other, thereby preventing reuse of the once-used puncture needle.

APPLICABILITY IN INDUSTRY

A puncture device according to the present invention can simplify the fabrication process thereof, and reduce the pain of the patient by reliably preventing plural times of punctures, and further, the user can remove a puncture needle cartridge from the puncture device without touching it. Therefore, it is useful in preventing infection.

Furthermore, a puncture needle cartridge according to the present invention is useful as a disposable puncture needle cartridge having a puncture needle for replacement of a puncture device used for blood collection or the like, and a puncture needle holder in which the puncture needle is movably stored, which holder can be replaced simultaneously with the puncture needle.

The invention claimed:

1. A puncture needle cartridge for installation in a puncture device, the puncture needle cartridge comprising:
   a lancet comprising an elongate lancet body having a puncture needle extending axially from one end of the body, and a portion to be held by a puncture device at the other end of the body, and a puncture needle protection cap for protecting the puncture needle; and
   a cylindrical puncture needle holder for holding the lancet body so that the lancet is movable axially in the holder, and the outer diameter of the puncture needle holder at its needle exit end is larger than the outer diameter of the puncture needle holder at its opposite end, with four linear grooves in the inner periphery of and parallel to the axial length of the puncture needle holder and evenly angularly spaced about a longitudinal axis of the holder;
   the lancet body comprises a first pair of convex portions diametrically opposite each other across a longitudinal axis of the lancet body,
   each of the first pair of convex portions, being slidably engaged with one of the grooves to thereby guide sliding movement of the lancet body,
   the lancet body further comprising a second pair of convex portions located diametrically opposite each other across the longitudinal axis of the lancet body and spaced axially separately from said first pair of convex portions, and located outside the puncture needle holder.

2. The puncture needle cartridge as defined in claim 1, wherein the periphery of the puncture needle holder is substantially cylindrical.

3. A puncture needle cartridge for installation in a puncture device, the puncture needle cartridge comprising:
   a lancet comprising an elongate lancet body having a puncture needle extending axially from one end of the body and a portion to be held by a puncture device at the other end of the body, and a puncture needle protection cap for protecting the puncture needle; and
   a cylindrical puncture needle holder for holding the lancet body so that the lancet body is movable axially in the holder, and the outer diameter of the puncture needle holder at its needle exit end is larger than the outer diameter of the puncture needle holder at its opposite end, with a plurality of linear grooves in the inner periphery of and parallel to the axial length of the puncture needle holder and evenly angularly spaced about a longitudinal axis of the holder;

the lancet body comprises a first pair of convex portions which are diametrically across a longitudinal axis of the lancet body, each one of the first pair of convex portions, being slidably engaged with one of said grooves to thereby guide sliding movement of the lancet body, the lancet body further comprising a second pair of convex portions located diametrically opposite each other across the longitudinal axis of the lancet body and spaced axially separately from said first pair of convex portions, and located outside the puncture needle holder.

* * * * *

UNITED STATES PATENT AND TRADEMARK OFFICE
CERTIFICATE OF CORRECTION

PATENT NO. : 8,740,923 B2  
APPLICATION NO. : 12/662279  
DATED : June 3, 2014  
INVENTOR(S) : Ono et al.

Page 1 of 1

It is certified that error appears in the above-identified patent and that said Letters Patent is hereby corrected as shown below:

On the title page item (63) should read:

--Related U.S. Application Data: Continuation of application No. 11/912,932, filed as application No. PCT/JP2006/308911 on Apr. 27, 2006, now abandoned.--

Signed and Sealed this
Seventeenth Day of February, 2015

Michelle K. Lee
*Deputy Director of the United States Patent and Trademark Office*